United States Patent [19]

Rentzea et al.

[11] Patent Number: 4,628,058
[45] Date of Patent: Dec. 9, 1986

[54] N-(2,3-DIHYDROBENZOFURAN-2-YL)-AZOLYLUREAS AND FUNGICIDES CONTAINING THESE COMPOUNDS

[75] Inventors: Costin Rentzea, Heidelberg; Stefan Karbach; Eberhard Ammermann, both of Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 713,642

[22] Filed: Mar. 19, 1985

[30] Foreign Application Priority Data

Mar. 24, 1984 [DE] Fed. Rep. of Germany ....... 3410925

[51] Int. Cl.$^4$ .................. A01N 47/38; C07D 405/12
[52] U.S. Cl. .................... 514/383; 514/397; 548/110; 548/262; 548/336; 549/462; 549/467
[58] Field of Search .......... 548/262, 336; 514/383, 514/397

[56] References Cited

U.S. PATENT DOCUMENTS 4,287,210 9/1981 Eckhardt et al. .................. 548/341

FOREIGN PATENT DOCUMENTS 0088380 9/1983 European Pat. Off. ........... 548/262
0156255 10/1985 European Pat. Off. ........... 548/262
1318590 7/1973 United Kingdom ............... 548/341

OTHER PUBLICATIONS

Chemical Week, Jun. 21, 1972, p. 46.

Primary Examiner—Alton D. Rollins
Attorney, Agent, or Firm—Keil & Weinkauf

[57] ABSTRACT

N-(2,3-dihydrobenzofuran-2-yl)-azolylureas of the formula

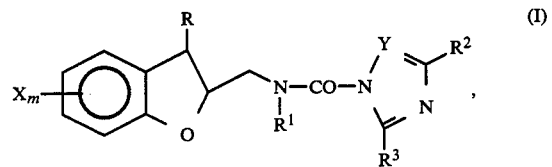

where R is hydrogen or alkyl, X is hydrogen, halogen, nitro, cyano, trifluoromethyl, alkyl, alkoxy, alkylthio, phenyl or phenoxy, m is an integer from 1 to 4, Y is CH or N, $R^1$ is alkyl, alkenyl, alkoxyalkyl, alkylthioalkyl, cycloalkyl or cycloalkylalkyl or an unsubstituted or substituted phenyl or benzyl radical, and $R^2$ and $R^3$ are each hydrogen or alkyl, and fungicides which contain these compounds.

4 Claims, No Drawings

N-(2,3-DIHYDROBENZOFURAN-2-YL)-AZOLYLUREAS AND FUNGICIDES CONTAINING THESE COMPOUNDS

The present invention relates to novel dihydrobenzofuran-2-yl azolylureas, processes for their preparation, and fungicidal agents which contain these compounds as active ingredients.

It has been disclosed that N-trichloromethylthiotetrahydrophthalimide can be used as a fungicide in agriculture and in fruit cultivation and horticulture (Chem. Week, June 21, 1972, page 46). It has also been disclosed that 1-(2-(2,4-dichlorophenyl)-2-(2-propenyloxy)-ethyl)-1H-imidazole can be used as a fungicide (GB No. 1,318,590). However, its action is unsatisfactory, particularly at low application rates.

It is an object of the present invention to provide more effective fungicidal active ingredients. The conventional agent can be used only prior to infection, and, at low application rates, its action does not meet practical requirements.

We have found that this object is achieved, and that dihydrobenzofuran-2-yl azolylureas of the formula

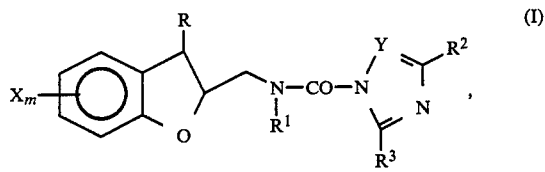

where R is hydrogen or alkyl of 1 to 4 carbon atoms, X is hydrogen, halogen, nitro, cyano, trifluoromethyl or alkyl, alkoxy or alkylthio, each of 1 to 4 carbon atoms, or phenyl or phenoxy, m is an integer from 1 to 4, the individual groups X being identical or different when m is greater than 1, and Y is CH or N, $R^1$ is alkyl, alkenyl, alkoxyalkyl, alkylthioalkyl, cycloalkyl or cycloalkylalkyl, each of not more than 12 carbon atoms, or phenyl or benzyl, each of which is unsubstituted or substituted by halogen, $C_1$–$C_4$-alkyl, $C_1$–$C_4$-alkoxy, trifluoromethyl, nitro or cyano, and $R^2$ and $R^3$ are identical or different and are each hydrogen or alkyl of 1 to 5 carbon atoms, are very effective against harmful fungi.

The novel compounds of the formula I contain chiral centers and are obtained in general in the form of racemates or as diastereomer mixtures. For some of the novel compounds, the diastereomers can be separated by, for example, column chromatography, or can be isolated in pure form on the basis of differences in solubility. Such pure diastereomers can be converted to the pure enantiomers by a conventional method. These, the analogous optically pure compounds, the racemates and the diastereomer mixtures are embraced by the present invention. When the novel compounds are used as fungicides, the pure diastereomers or enantiomers as well as the mixtures of these which are obtained in the synthesis can be employed; the mixtures are preferably used.

X is preferably hydrogen, fluorine, chlorine, bromine, cyano, nitro, trifluoromethyl, methyl, ethyl, n-propyl, isopropyl, n-butyl, isobutyl, sec.-butyl, tert.-butyl, methoxy, ethoxy, methylthio, phenyl or phenoxy.

In formula I, examples of suitable radicals $R^1$ are methyl, ethyl, n-propyl, n-butyl, is O butyl, sec.-butyl, n-pentyl, 3-methylbut-1-yl, 2-methylbut-1-yl, pent-3-yl, n-hexyl, 3,3-dimethylbut-1-yl, 2,2,3-trimethylprop-1-yl, n-heptyl, n-octyl, 2,4,4-trimethylpentyl, 2-ethylhexyl, n-nonyl, 3,5,5-trimethylhexyl, 2-isopropyl-5-methylhexyl, 2-isopropyl-5-methylhexyl, n-decyl, 3,7-dimethyloctyl, dodecyl, cyclopropylmethyl, cyclopentyl, cyclohexyl, cyclohexylmethyl, 4-methylcyclohexyl, 4-tert.-butylcyclohexyl, 4-methoxycyclohexyl, 2-methoxyethyl, 2-ethoxyethyl, 2-propoxyethyl, 2-butoxyethyl, 2-hexyloxyethyl, 3-methoxypropyl, 3-ethoxypropyl, 3-propoxypropyl, 3-butoxypropyl, 3-hexyloxypropyl, 2-methylthioethyl, 2-ethylthioethyl, 2-propylthioethyl, 2-butylthioethyl, 3-methylthiopropyl, 3-ethylthiopropyl, 3-propylthiopropyl, allyl, 2-methylallyl, but-2-en-1-yl, pent-2-en-1-yl, phenyl, 4-fluorophenyl, 4-chlorophenyl, 2,4-dichlorophenyl, 3,4-dichlorophenyl, 4-bromophenyl, 4-methylphenyl, 4-tert.-butylphenyl, 4-methoxyphenyl, 4-ethoxyphenyl, 4-trifluoromethylphenyl, 4-cyanophenyl, benzyl, 4-fluorobenzyl, 4-chlorobenzyl, 3,4-dichlorobenzyl, 2,4-dichlorobenzyl, 4-bromobenzyl, 4-methylbenzyl, 4-tert.-butylbenzyl, 4-methoxybenzyl, 3- and 4-trifluoromethylbenzyl and 4-ethoxybenzyl.

R, $R^2$ and $R^3$ are each preferably hydrogen, methyl, ethyl, n-propyl or isopropyl.

Y is nitrogen or CH and m is an integer from 1 to 4.

The compounds of the formula I can be prepared by a method in which a carbamyl chloride of the formula II

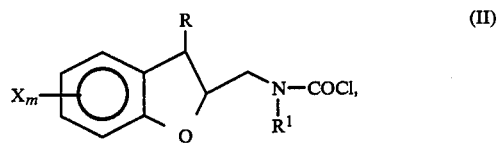

where R, $R^1$ and $X_m$ have the above meanings, (a) is reacted with an azole of the formula III

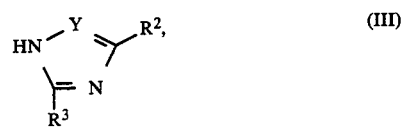

where $R^2$, $R^3$ and Y have the above meanings, or (b) is reacted with a metal derivative of this, of the formula IV

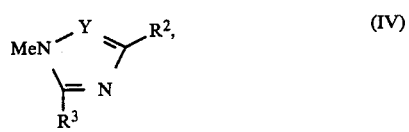

where $R^2$, $R^3$ and Y have the above meanings and Me is lithium, sodium, potassium or one equivalent of calcium, or (c) is reacted with a silyl derivative of this, of the formula V

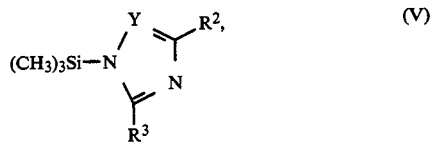

where $R^2$, $R^3$ and Y have the above meanings.

Reaction (a) is carried out in the presence or absence of a solvent or diluent and with or without the addition of an inorganic or organic base or of a reaction accelerator, at from 10° to 120° C.

Examples of preferred solvents or diluents which are inert to the reactants are aliphatic or aromatic hydrocarbons and halohydrocarbons, such as n-pentane, cyclohexane, methylene chloride, 1,1,1-trichloroethane, benzene, toluene, xylene or chlorobenzene, aliphatic ketones, such as acetone, methyl ethyl ketone or diethyl ketone, ethers, such as diethyl ether, methyl tert.-butyl ether, dimethoxyethane, tetrahydrofuran or dioxane, esters, such as ethyl acetate, nitriles, such as acetonitrile, amides, such as dimethylformamide, dimethylacetamide and N-methylpyrrolidone, and mixtures of these.

Examples of suitable bases which, if required, may also be used as acid acceptors in the reaction are alkali metal hydroxides, such as lithium hydroxide, sodium hydroxide, potassium hydroxide or calcium hydroxide, alkali metal carbonates, such as sodium carbonate, potassium carbonate, sodium bicarbonate or potassium bicarbonate, and amines, such as triethylamine, tripropylamine, N-methylpyrrolidine, N-methylpiperidine, N,N'-tetramethylethylenediamine, N,N-dimethylaniline, N,N-diethylaniline, pyridine or 4-dimethylaminopyridine. Other conventional bases may also be used.

Preferred reaction accelerators are metal halides, such as sodium iodide or potassium iodide, quaternary ammonium salts, such as tetrabutylammonium chloride, bromide or iodide or benzyltriethylammonium chloride or bromide, and crown ethers, such as 12-crown-4, 15-crown-5, 18-crown-6 or dibenzo-18-crown-6.

Reactions (b) and (c) are carried out in the presence or absence of a solvent or diluent, at from 0° to 40° C., preferably from 0° to 100° C. Suitable solvents for these reactions are those which can be used for process (a).

The compounds of the formula I can furthermore be prepared by reacting a secondary amine of the formula VI

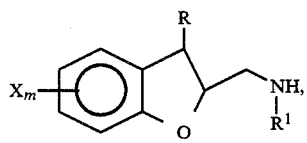

where R, $R^1$ and $X_m$ have the above meanings, with a carbonyl-bisazole of the formula VII

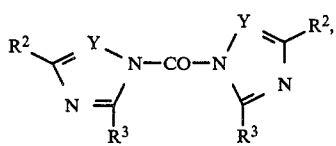

where $R^2$, $R^3$ and Y have the above meanings, in the presence or absence of a solvent or diluent and with or without the addition of a reaction accelerator.

Examples of suitable solvents or diluents for this purpose are diethyl ether, 1,2-dimethoxyethane, dipropyl ether, dibutyl ether, methyl tert.-butyl ether, tetrahydrofuran, dimethoxyethane, anisole, n-pentane, n-hexane, n-heptane, n-octane, isooctane, cyclohexane, toluene, chlorobenzene, xylenes, acetonitrile, ethyl acetate, dimethylformamide, N-methylpyrrolidone, acetone and methyl ethyl ketone.

Examples of suitable reaction accelerators are 4-dimethylaminopyridine and 4-pyrrolidinopyridine.

The starting materials of the formula II can readily be prepared by conventional processes, for example by reacting an amine of the formula VI with phosgene (Houben-Weyl-Müller, Methoden der organischen Chemie, volume 8, pages 115–118, Georg Thieme Verlag, Stuttgart, 1952).

Finally, the secondary amines of the formula VI are prepared by reacting a known amine of the formula $R^1NH_2$, where $R^1$ has the above meanings, with a 2,3-dihydrobenzofuran-2-ylmethyl halide (cf. Toyashima et al., Yakugaku Zasshi, 88 (1968), 503) of the formula VIII

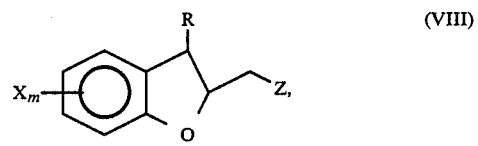

where R and $X_m$ have the above meanings and Z is chlorine or bromine, in the presence or absence of a strong inorganic or organic base and in the presence or absence of a solvent or diluent.

The Examples which follow illustrate the preparation of the compounds of the formula I.

EXAMPLE 1

(a) 33 g (0.118 mole) of 5,7-dichloro-2,3-dihydrobenzofuran-2-ylmethyl bromide and 200 ml of n-butylamine were stirred for 12 hours at 60° C. The mixture was evaporated down under reduced pressure, 100 ml of a 20% strength aqueous sodium hydroxide solution were added to the residue, and the mixture was then extracted by shaking with 300 ml of methylene chloride. The organic phase was washed with three times 70 ml of water, dried and evaporated down, the residue was dissolved in 300 ml of dry diethyl ether, the solution was gassed with dry hydrogen chloride at from 0° to +3° C., and the colorless crystalline precipitate was filtered off under suction, washed with dry diethyl ether and dried. 27 g of N-(5,7-dichloro-2,3-dihydrobenzofuran-2-ylmethyl)-N-butylamine hydrochloride of melting point 202°–205° C. were obtained.

(b) A thoroughly stirred suspension of 26 g (0.0838 mole) of N-(5,7-dichloro-2,3-dihydrobenzofuran-2-ylmethyl)-N-butylamine hydrochloride in 250 ml of dry ethyl acetate was gassed with phosgene at 50° C. After 4 hours, the suspended material had dissolved. The mixture was evaporated down under reduced pressure, at 50° C. and under 0.5 mbar in the final stage. 27 g of N-(5,7-dichloro-2,3-dihydrobenzofuran-2-ylmethyl)-N-butylcarbamyl chloride were obtained as a colorless oil, which was reacted further without additional purification.

(c) 13.5 g (0.04 mole) of N-(5,7-dichloro-2,3-dihydrobenzofuran-2-ylmethyl)-N-butylcarbamyl chloride were added dropwise to a solution of 6.8 g (0.1 mole) of imidazole in 150 ml of dry tetrahydrofuran at 20° C. The mixture was stirred for 6 hours at 70° C., after which it was cooled to 20° C., and the resulting precipitate was filtered off under suction. The filtrate was evaporated down under reduced pressure, the residue was dissolved in 200 ml of methylene chloride, the solution was washed with three times 80 ml of water, dried and evaporated down, the resin which remained was left to stand for 3 hours at 0° C. with 30 ml of diethyl ether, and the crystals formed were filtered off under suction. 12.8 g of 1-(N-(5,7-dichloro-2,3-dihydrobenzofuran-2-ylmethyl)-N-butylcarbamyl)imidazole of melting point 98°–100° C. were obtained (compound No. 1).

EXAMPLE 2

13.5 g (0.04 mole) of N-(5,7-dichloro-2,3-dihydrobenzofuran-2-ylmethyl)-N-butylcarbamyl chloride were added dropwise to a suspension of 5.5 g (0.06 mole) of sodium 1,2,4-triazolide in 120 ml of dry tetrahydrofuran at 20° C. The mixture was stirred for 6 hours at 65° C., after which it was cooled to 20° C., and the precipitate was filtered off under suction. The filtrate was evaporated down, the residue was suspended in 30 ml of diethyl ether, and the product was filtered off under suction. 13.1 g of 1-(N-(5,7-dichloro-2,3-dihydrobenzofuran-2-ylmethyl)-N-butylcarbamyl)-1,2,4-triazole were obtained as colorless crystals of melting point 122°–124° C. (compound NO. 2).

The compounds listed in the Table below can be prepared in a similar manner:

| Ex. no. | $X_m$ | R | $R^1$ | Y | $R^2$ | $R^3$ | M.p [°C.] IR (film) cm$^{-1}$ |
|---|---|---|---|---|---|---|---|
| 3 | H | H | n-$C_3H_7$ | CH | H | H | 1693, 1480, 1462, 1418, 1296, 1232, 1100, 1070, 1002, 753, 658 |
| 4 | H | H | n-$C_3H_7$ | N | H | H | 72–74 |
| 5 | H | H | —$(CH_2)_2$—O—$C_2H_5$ | CH | H | H | |
| 6 | H | $CH_3$ | —$(CH_2)_2$—O—$C_3H_7$-n | CH | H | H | |
| 7 | H | $CH_3$ | —$(CH_2)_2$—O—$C_6H_{13}$-n | CH | H | H | |
| 8 | H | $C_2H_5$ | —$(CH_2)_3$—O—$CH_3$ | CH | H | H | |
| 9 | H | $C_2H_5$ | —$(CH_2)_3$—$OC_2H_5$ | CH | H | H | |
| 10 | H | H | —$(CH_2)_3$—$OC_2H_5$ | CH | H | H | |
| 11 | H | H | —$(CH_2)_3$—$OC_3H_7$ | CH | H | H | |
| 12 | H | H | cyclohexyl | CH | H | H | 88–90 |
| 13 | H | H | cyclohexyl | N | H | H | 2932, 1698, 1481, 1462, 1420, 1374, 1227, 1183, 1016, 991, 750, 660 |
| 14 | H | H | n-$C_3H_7$ | C—$CH_3$ | $CH_3$ | $CH_3$ | 2963, 1691, 1646, 1481, 1463, 1362, 1230, 1100, 1017, 872, 751 |
| 15 | H | H | n-$C_6H_{13}$ | CH | | H | 2955, 1694, 1481, 1418, 1295, 1282, 1230, 1000, 752, 658 |
| 16 | H | H | n-$C_6H_{13}$ | N | N | H | 2929, 1701, 1480, 1463, 1424, 1380, 1277, 1230, 992, 872, 750 |
| 17 | H | H | —$CH_2$—CH=CH—$CH_3$ | CH | H | H | |
| 18 | H | H | —$CH_2$—CH=CH—$CH_3$ | N | H | H | |
| 19 | H | H | —$CH_2$—CH=CH—$C_3H_7$ | CH | H | H | |
| 20 | H | H | $C_6H_5$ | CH | H | H | |
| 21 | H | H | $C_6H_5$ | N | H | H | |
| 22 | H | H | 4-$CH_3$—$C_6H_4$— | CH | H | H | |
| 23 | 5-F | H | n-$C_6H_{13}$ | CH | H | H | |
| 24 | 5-F | H | n-$C_6H_{13}$ | N | H | H | |
| 25 | 5-Cl | H | n-$C_6H_{13}$ | CH | H | H | |
| 26 | 5-Cl | H | n-$C_6H_{13}$ | N | H | H | |
| 27 | 5,7-$Cl_2$ | H | n-$C_3H_7$ | CH | H | H | 108–110 |
| 28 | 5,7-$Cl_2$ | H | n-$C_3H_7$ | N | H | H | 99–101 |
| 29 | 5,7-$Cl_2$ | H | iso-$C_4H_9$ | CH | H | H | 131–132 |
| 30 | 5,7-$Cl_2$ | H | iso-$C_4H_9$ | N | H | H | 73–75 |
| 31 | 5,7-$Cl_2$ | H | sec-$C_4H_9$ | CH | H | H | 1698, 1462, 1378, 1300, 1275, 1197, 991, 762, 670 |
| 32 | 5,7-$Cl_2$ | H | sec-$C_4H_9$ | N | H | H | 1676, 1460, 1413, 1375, 1334, 1300, 1161, 996, 851, 758 |
| 33 | 5,7-$Cl_2$ | H | n-$C_6H_{13}$ | CH | H | H | 80–82 |
| 34 | 5,7-$Cl_2$ | H | n-$C_6H_{13}$ | N | H | H | 79–82 |
| 35 | 5,7-$Cl_2$ | H | —$(CH_2)_3$—O—$C_4H_9$-iso | CH | H | H | 61–63 |
| 36 | 5,7-$Cl_2$ | H | —$(CH_2)_3$—O—$C_4H_9$-iso | N | H | H | 90–92 |
| 37 | 5,7-$Cl_2$ | H | —$CH_2$—CH($C_2H_5$)—$C_4H_9$-n | CH | H | H | 121–123 |
| 38 | 5,7-$Cl_2$ | H | —$(CH_2)_2$—CH($CH_3$)—C($CH_3$)$_3$ | CH | H | H | 84–85 |
| 39 | 5,7-$Cl_2$ | H | —$(CH_2)_2$—CH($CH_3$)—C($CH_3$)$_3$ | N | H | H | $n_D^{26}$ = 1.5340 |
| 40 | 5,7-$Cl_2$ | H | —$CH_2$—CH($C_2H_5$)—$C_4H_9$-n | N | H | H | 50–53 |
| 41 | 5,7-$Cl_2$ | H | —$CH_2$-cyclopropyl | CH | H | H | 114–116 |
| 42 | 5,7-$Cl_2$ | H | —$CH_2$-cyclopropyl | N | H | H | 86–88 |
| 43 | 5,7-$Cl_2$ | H | —$(CH_2)_2$—O—$CH_3$ | CH | H | H | 84–86 |
| 44 | 5,7-$Cl_2$ | H | —$(CH_2)_2$—O—$CH_3$ | N | H | H | 129–132 |
| 45 | 5,7-$Cl_2$ | H | —$(CH_2)_2$—S—$CH_3$ | CH | H | H | 67–120 |
| 46 | 5,7-$Cl_2$ | H | —$(CH_2)_2$—S—$CH_3$ | N | H | H | 118–120 |
| 47 | 5,7-$Cl_2$ | H | —$CH_2$—CH=$CH_2$ | CH | H | H | 113–115 |
| 48 | 5,7-$Cl_2$ | H | —$CH_2$—CH=$CH_2$ | N | H | H | 83–85 |
| 49 | 5-Br, 7-Cl | H | n-$C_4H_9$ | N | H | H | |
| 50 | 5-Br, 7-Cl | H | n-$C_4H_9$ | CH | H | H | 98–100 |
| 51 | 4,6-$Cl_2$ | H | n-$C_6H_{13}$ | CH | H | H | |
| 52 | 4,6-$Cl_2$ | H | n-$C_6H_{13}$ | N | H | H | |
| 53 | 5-$CH_3$ | H | n-$C_6H_{13}$ | CH | H | H | |

-continued

| Ex. no. | $X_m$ | R | $R^1$ | Y | $R^2$ | $R^3$ | M.p [°C.] IR (film) cm$^{-1}$ |
|---|---|---|---|---|---|---|---|
| 54 | 5-CH$_3$ | H | n-C$_6$H$_{13}$ | N | H | H | |
| 55 | 5-tert-C$_4$H$_9$ | H | n-C$_6$H$_{13}$ | CH | H | H | |
| 56 | 5-tert-C$_4$H$_9$ | H | n-C$_6$H$_{13}$ | N | H | H | |
| 57 | 5-CH$_3$O— | H | n-C$_6$H$_9$ | CH | H | H | 1696, 1494, 1446, 1252, 1233, 1197, 995, 846, 823, 768 |
| 58 | 5-CH$_3$O— | H | n-C$_4$H$_9$ | N | H | H | 1700, 1489, 1429, 1380, 1277, 1219, 1203, 1183, 1047, 993, 810, 744 |
| 59 | 5-C$_2$H$_5$—O— | H | n-C$_6$H$_{13}$ | CH | H | H | |
| 60 | 5-C$_2$H$_5$—O— | H | n-C$_6$H$_{13}$ | N | H | H | |
| 61 | 5-CH$_3$O | H | n-C$_6$H$_{13}$ | CH | H | H | 1703, 1496, 1457, 1417, 1296, 1251, 1234, 1189, 1000, 850, 822 |
| 62 | 5-CH$_3$O— | H | n-C$_6$H$_{13}$ | N | H | H | 1700, 1488, 1468, 1430, 1380, 1276, 1204, 1134, 1030, 992, 740 |
| 63 | H | H | —CH(CH$_3$)C$_5$H$_{11}$-$n$ | CH | H | H | 2929, 1697, 1481, 1461, 1416, 1377, 1229, 991, 750 |
| 64 | H | H | —CH(CH$_3$)C$_5$H$_{11}$-$n$ | N | H | H | 2955, 1692, 1480, 1408, 1370, 1234, 1099, 752 |
| 65 | H | H | cyclooctyl | CH | H | H | 2922, 1693, 1480, 1448, 1276, 1232, 1068, 1000, 751 |
| 66 | H | H | cyclooctyl | N | H | H | 2922, 1700, 1480, 1462, 1377, 1228, 993, 749, 670 |

The novel compounds have an excellent action on a broad spectrum of plant-pathogenic fungi, especially from the Ascomycetes and Basidiomycetes classes. Some of them have a systemic action and can be used as soil or foliar fungicides. They may also be used for protecting materials, e.g., for combatting wood-destroying fungi such as Coniophora puteana and Polystictus versicolor. The novel active ingredients also combat wood-discoloring fungi such as Pullularia pullulans, and molds.

The fungicidal compounds are particularly interesting for combatting numerous fungi in various crops or their seeds, especially wheat, rye, barley, oats, rice, Indian corn, cotton, soybeans, coffee, sugarcane, fruit, ornamentals in horticulture, and vegetables, such as cucumbers, beans and Cucurbitaceae.

The new compounds are particularly suitable for combatting the following plant diseases: Pseudocercosporella herpotrichoides in cereals, Erysiphe cichoriacearum in Cucurbitaceae, Podosphaera leucotricha in apples, Uncinula necator in grapes, Puccinia species in cereals, Rhizoctonia solani in cotton, Ustilago species in cereals and sugarcane, Venturia inaequalis (scab) in apples, Septoria nodorum in wheat, Botrytis cinerea in strawberries and grapes, Rhynchosporium secalis and Pyrenophora teres in cereals.

The active ingredients can suppress, simultaneously, the growth of 2 or more of the said fungi, and are excellently tolerated by plants. Some of the active ingredients also have curative properties, i.e., the agents may be applied after infection of the plants by the pathogen and success is still ensured.

The fungicidal agents contain from 0.1 to 95, and preferably from 0.5 to 90, wt % of active ingredient. The application rates depend on the type of effect desired, and range from 0.1 to 5 kg of active ingredient per hectare.

The novel active ingredients may also be mixed and applied with other active ingredients, e.g., herbicides, insecticides, growth regulators, other fungicides and fertilizers. When mixed with other fungicides, the spectrum of fungicidal action is in many cases increased; with a number of these fungicidal compositions, synergistic effects also occur, i.e., the fungicidal action of the combination product is greater than the effect of the individual components added together. Examples of fungicides which can be combined with the novel compounds are as follows:
sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate
and
N,N'-polyethylene-bis-(thiocarbamoyl)-disulfide ammonia complex of zinc-(N,N'-propylene-bisdithiocarbamate)
and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carbox-amide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-forma-mide
1-(3,4-dichloroanilino)-1-formylamino-2,2,2-trichlore-thane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidine-methanol
5-butyl-2-dimethylamino-4-hydroxy-6-methylpyrimi-dine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-ala-nate
methyl D,L-N-(2,6-dimethylphenyl)-N-(2-methox-yacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidin-2,4-dione
3-(3,5-dichlorophenyl)-1-isopropyl-carbamoylhydan-toin
N-(3,5-dichlorophenyl)-1,2-dimethyl-cyclopropane-1,2-dicarboximide
2-cyano-N-(ethylaminocarbonyl)-2-(methoximino)-acetamide
1-(2-(2,4-dichlorophenyl)-pentyl)-1H-1,2,4-triazole
2,4-difluoro-alpha-(1H-1,2,4-triazolyl-1-methyl)-benz-hydryl alcohol.

The novel active ingredients are applied for instance in the form of directly sprayable solutions, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be used direct or after emulsification in water, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of such formulations follow.

I. 90 parts by weight of compound no. 31 is mixed with 100 parts by weight of N-methyl-alpha-pyrrolidone. A mixture is obtained which is suitable for application in the form of very fine drops.

II. 20 parts by weight of compound no. 12 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 15 is dissolved in a mixture consisting of 30 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 16 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 20 parts by weight of compound no. 28 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in water, a spray liquor is obtained.

VI. 5 parts by weight of compound no. 30 is intimately mixed with 95 parts by weight of particulate kaolin. A dust is obtained containing 5% by weight of the active ingredient.

VII. 30 parts by weight of compound no. 31 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 43 is intimately mixed with 30 parts of the sodium salt of a phenolsulfonic acid-urea-formaldehyde condensate, 2 parts of silica gel and 48 parts of water to give a stable aqueous dispersion.

IX. 20 parts of compound no. 44 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following experiments demonstrate the biological action of the novel compounds. Comparative agent (A) is N-trichloromethylthiotetrahydrophthalimide suitable for combatting Botrytis and disclosed on p. 46 of Chem. Week, June 21, 1972. Comparative agent (B) is 1-(2-(2,4-dichlorophenyl)-2-(2-propenyloxy)-ethyl)-1H-imidazole (British No. 1,318,590).

EXPERIMENT 1

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated control plants that the necroses covered the major portion of the leaves.

The results of this experiment show that for instance compound no. 31, applied as a 0.05% spray, had a better fungicidal action (e.g., 90%) than prior art active ingredient A (e.g. 70%).

EXPERIMENT 2

Action on *Pyricularia oryzae*

Leaves of pot-grown rice seedlings of the "Bahia" variety were sprayed with aqueous emulsions containing (dry basis) 80% of active ingredient and 20% of emulsifier, and inoculated 24 hours later with an aqueous spore suspension of *Pyricularia oryzae*. The test plants were set up in climatic cabinets at 22° to 24° C. and a relative humidity of 95 to 99%. The spread of the disease was assessed after 7 days.

The results of this experiment show that active ingredients nos. 12, 15, 16, 28, 30, 31, 43, 44 and 48, applied for instance as 0.05% sprays, had a good fungicidal action (e.g., 90%).

EXPERIMENT 3

Action on leaf rust of wheat

Leaves of pot-grown wheat seedlings of the "Jubilar" variety were dusted with spores of rust (*Puccinia recondita*). The pots were then placed in a high humidity (90–95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient and 20% of emulsifier. After the spray coating had dried, the test plants were set up in a greenhouse at from 20° to 22° C. and from 65 to 70% relative humidity. After 8 days, the degree of development of the rust fungi on the leaves was determined.

The results of this experiment show that active ingredients 27, 29 and 31, applied as 0.05% sprays, had a better fungicidal action (e.g., 97%) than prior art active ingredient B (e.g., 70%).

EXPERIMENT 4

Action on eyespot disease in wheat

Leaves of pot-grown wheat seedlings of the "Jubilar" variety were sprayed to runoff with aqueous emulsions containing (dry basis) 80% of active ingredient and 20% of emulsifier, and inoculated 24 hours later with an aqueous spore suspension of the eyespot pathogen (*Pseudocercosporella herpotrichoides*). The test plants were then set up in climatic cabinets at 8° to 10° C. and a relative humidity of 95 to 99%. After 3 to 4 weeks most of the untreated control plants exhibited clear symptoms of the disease, which meant that the experiment could be evaluated.

The results show that active ingredient 15, applied for instance as a 0.01% spray, had a good fungicidal action (e.g., 90%).

We claim:

1. An N-((2,3-dihydrobenzofuran)-2-yl)-azolylurea of the formula

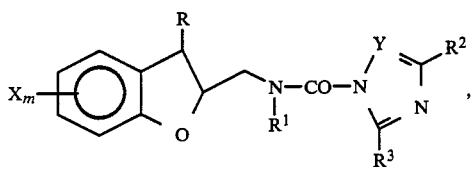

where R is hydrogen or alkyl of 1 to 4 carbon atoms, X is hydrogen, halogen, nitro, cyano, trifluoromethyl or alkyl, alkoxy or alkylthio, each of 1 to 4 carbon atoms, or phenyl or phenoxy, m is an integer from 1 to 4, the individual groups X being identical or different when m is greater than 1, and Y is CH or N, $R^1$ is alkyl, alkenyl, alkoxyalkyl, alkylthioalkyl, cycloalkyl or cycloalkylalkyl, each of not more than 12 carbon atoms, or phenyl or benzyl, each of which is unsubstituted or substituted by halogen, $C_1$-$C_4$-alkyl, $C_1$-$C_4$-alkoxy, trifluoromethyl, nitro or cyano, and $R^2$ and $R^3$ are identical or different and are each hydrogen or alkyl of 1 to 5 carbon atoms.

2. A dihydrobenzofuran-2-yl-azolylurea of the formula I as set forth in claim 1, where X is hydrogen, fluorine, chlorine, bromine, cyano, nitro, trifluoromethyl, methyl, ethyl, n-propyl, isopropyl, n-butyl, isobutyl, sec-butyl, tert-butyl, methoxy, ethoxy, methylthio, phenyl or phenoxy, R, $R^2$ and $R^3$ are hydrogen, methyl, ethyl, n-propyl or isopropyl, Y is CH or N, $R^1$ is methyl, ethyl, n-propyl, n-butyl, isobutyl, sec-butyl, n-pentyl, 3-methylbut-1-yl, 2-methylbut-1-yl, pent-3-yl, n-hexyl, 3,3-dimethylbut-1-yl, 2,2,3-trimethylprop-1-yl, n-heptyl, n-octyl, 2,4,4-trimethylpentyl, 2-ethylhexyl, n-nonyl, 3,5,5-trimethylhexyl, 2-isopropyl-5-methylhexyl, n-decyl, 3,7-dimethyloctyl, cyclopropylmethyl, cyclopentyl, cyclohexyl, cyclohexylmethyl, 4-methylcyclohexyl, 2-methoxyethyl, 2-ethoxyethyl, 2-propoxyethyl, 2-butoxyethyl, 3-methoxypropyl, 3-ethoxypropyl, 3-propoxypropyl, 3-butoxypropyl, 2-methylthioethyl, 2-ethylthioethyl, 3-methylthiopropyl, allyl, but-2-en-1-yl, pent-2-en-1-yl, phenyl, p-chlorophenyl, p-methoxyphenyl, p-methylphenyl, benzyl, p-chlorobenzyl, 2,4-dichlorbenzyl or p-methylbenzyl, and m is an integer from 1 to 4.

3. A fungicidal agent containing an inert additive and an effective amount of an N-((2,3-dihydrobenzofuran)-2-yl)-azolylurea of the formula

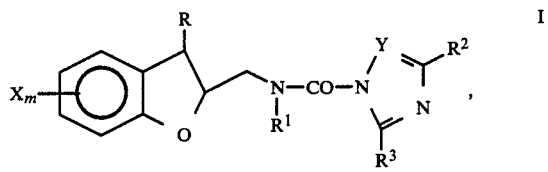

where R is hydrogen or alkyl or 1 to 4 carbon atoms, X is hydrogen, halogen, nitro, cyano, trifluoromethyl or alkyl, alkoxy or alkylthio, each of 1 to 4 carbon atoms, or phenyl or phenoxy, m is an integer from 1 to 4, the individual groups X being identical or different when m is greater than 1, and Y is CH or N, $R^1$ is alkyl, alkenyl, alkoxyalkyl, alkylthioalkyl, cycloalkyl or cycloalkylalkyl, each of not more than 12 carbon atoms, or phenyl or benzyl, each of which is unsubstituted or substituted by halogen, $C_1$-$C_4$-alkyl, $C_1$-$C_4$-alkoxy, trifluoromethyl, nitro or cyano, and $R^2$ and $R^3$ are identical or different and are each hydrogen or alkyl of 1 to 5 carbon atoms.

4. A process for combatting fungi, wherein the fungi or the materials, areas, plants or seed threatened by fungus attack are treated with a fungicidally effective amount of an N-((2,3-dihydrobenzofuran)-2-yl)-azolylurea of the formula

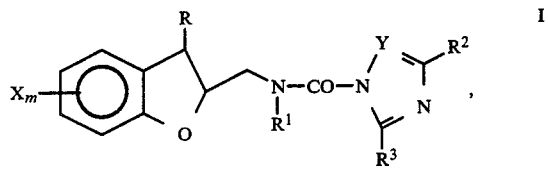

where R is hydrogen or alkyl of 1 to 4 carbon atoms, X is hydrogen, halogen, nitro, cyano, trifluoromethyl or alkyl, alkoxy or alkylthio, each of 1 to 4 carbon atoms, or phenyl or phenoxy, m is an integer from 1 to 4, the individual groups X being identical or different when m is greater than 1, and Y is CH or N, $R^1$ is alkyl, alkenyl, alkoxyalkyl, alkylthioalkyl, cycloalkyl or cycloalkylalkyl, each of not more than 12 carbon atoms, or phenyl or benzyl, each of which is unsubstituted or substituted by halogen, $C_1$-$C_4$-alkyl, $C_1$-$C_4$-alkoxy, trifluoromethyl, nitro or cyano, and $R^2$ and $R^3$ are identical or different and are each hydrogen or alkyl of 1 to 5 carbon atoms.

* * * * *